United States Patent
Jackson et al.

(10) Patent No.: US 10,060,886 B2
(45) Date of Patent: Aug. 28, 2018

(54) METHOD FOR HIGH PRESSURE GRADIENT CHROMATOGRAPHY USING PUMP STROKE CONTROL

(71) Applicant: Waters Technologies Corporation, Milford, MA (US)

(72) Inventors: Michael R. Jackson, Woonsocket, RI (US); Christopher Seith, Franklin, MA (US); Joshua A. Shreve, Franklin, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 551 days.

(21) Appl. No.: 14/612,532

(22) Filed: Feb. 3, 2015

(65) Prior Publication Data
US 2015/0219603 A1 Aug. 6, 2015

Related U.S. Application Data

(60) Provisional application No. 61/936,385, filed on Feb. 6, 2014.

(51) Int. Cl.
*G01N 30/34* (2006.01)
*F04B 23/04* (2006.01)
*F04B 49/06* (2006.01)

(52) U.S. Cl.
CPC ............ *G01N 30/34* (2013.01); *F04B 23/04* (2013.01); *F04B 49/065* (2013.01)

(58) Field of Classification Search
None
See application file for complete search history.

(56) References Cited

U.S. PATENT DOCUMENTS 3,985,019 A * 10/1976 Boehme .................. F04B 49/20
                                                                210/198.2
3,985,021 A * 10/1976 Achener ................ G01N 30/34
                                                                210/198.2

(Continued)

FOREIGN PATENT DOCUMENTS

EP          0299396         1/1989
GB          1450400         9/1976

(Continued)

OTHER PUBLICATIONS

Uleh, C.A., "Wet Gas Flow Metering Using PIV and Tracer Dilution", 2011, $3^{rd}$ IEEE Intl Conf on Adaptive Science and Technology (ICAST 2011).*

(Continued)

*Primary Examiner* — Mohammad Ali
*Assistant Examiner* — Kelvin Booker
(74) *Attorney, Agent, or Firm* — Schmeiser, Olsen & Watts LLP; William G. Guerin

(57) ABSTRACT

Described is a method of generating a flow having a composition gradient such as a mobile phase gradient for liquid chromatography. A pair of pumps is operated such that the initiations of pump strokes for one pump are controlled to occur between the initiations of pump strokes for the other pump so that the sequences of pump strokes fort the two pumps are interspersed in time. Initiations of the pump strokes of the second pump are offset in time relative to initiations of the pump strokes of the first pump such that variations in the flow rates of the first and second pumps due to initiation do not overlap in time. The volume of liquid contributed by a pump stroke is controlled according to the relative contribution of the respective pump to the composition gradient.

15 Claims, 4 Drawing Sheets

(56) References Cited

U.S. PATENT DOCUMENTS

| | | | | |
|---|---|---|---|---|
| 4,045,343 A * | 8/1977 | Achener | F04B 49/20 | 210/101 |
| 4,191,649 A * | 3/1980 | Hartwick | B01D 15/166 | 210/198.2 |
| 4,595,496 A * | 6/1986 | Carson | G01N 30/34 | 210/101 |
| 4,624,625 A * | 11/1986 | Schrenker | F04B 43/067 | 417/20 |
| 4,767,279 A * | 8/1988 | Dourdeville | F04B 49/065 | 210/101 |
| 4,882,063 A * | 11/1989 | Allington | G01N 30/34 | 210/101 |
| 4,954,253 A * | 9/1990 | Alexandrov | G01N 30/34 | 137/605 |
| 4,964,985 A * | 10/1990 | Goulder | F04B 11/0058 | 210/101 |
| 4,980,059 A * | 12/1990 | Barlow | G01N 30/36 | 210/101 |
| 4,981,597 A * | 1/1991 | Allington | G01N 30/34 | 210/101 |
| 4,988,447 A * | 1/1991 | Hellinger | G01N 30/32 | 210/198.2 |
| 4,990,250 A * | 2/1991 | Hellinger | G01N 30/32 | 210/101 |
| 5,071,562 A * | 12/1991 | Allington | G01N 30/34 | 210/101 |
| 5,080,785 A * | 1/1992 | Allington | G01N 30/34 | 210/101 |
| 5,135,658 A * | 8/1992 | Lee | G01N 30/34 | 210/101 |
| 5,158,675 A * | 10/1992 | Allington | G01N 30/34 | 137/88 |
| 5,234,587 A * | 8/1993 | Allington | G01N 30/34 | 210/101 |
| 5,253,981 A * | 10/1993 | Yang | F04B 9/047 | 210/101 |
| 5,360,320 A * | 11/1994 | Jameson | G01N 30/34 | 210/101 |
| 5,393,434 A * | 2/1995 | Hutchins | F04B 7/0076 | 210/101 |
| 5,423,661 A * | 6/1995 | Gabeler | F04C 14/08 | 210/101 |
| 5,630,706 A * | 5/1997 | Yang | B01F 13/0827 | 210/198.2 |
| 5,635,070 A * | 6/1997 | Allington | B01D 11/0203 | 210/416.1 |
| 5,637,208 A * | 6/1997 | Dourdeville | F04B 7/0007 | 137/565.13 |
| 5,664,938 A * | 9/1997 | Yang | B01F 13/0827 | 137/114 |
| 6,299,767 B1 * | 10/2001 | Dourdeville | B01D 15/166 | 210/101 |
| 6,427,526 B1 * | 8/2002 | Davison | B01D 15/12 | 210/656 |
| 6,561,767 B2 * | 5/2003 | Berger | | 417/279 |
| 7,631,542 B2 * | 12/2009 | Weissgerber | G01N 30/36 | 73/61.56 |
| 9,744,477 B2 * | 8/2017 | Almeida | B01D 15/18 | |
| 9,770,678 B2 * | 9/2017 | Jackson | B01D 19/0073 | |
| 9,970,908 B2 * | 5/2018 | Yotani | G01N 30/34 | |
| 2002/0116989 A1 * | 8/2002 | Davison | B01D 15/12 | 73/61.55 |
| 2002/0134143 A1 * | 9/2002 | Allington | B01D 15/12 | 73/61.58 |
| 2003/0026704 A1 * | 2/2003 | Berger | G01N 30/32 | 417/53 |
| 2003/0116195 A1 * | 6/2003 | Weissgerber | G01N 30/36 | 137/487.5 |
| 2003/0118459 A1 * | 6/2003 | Gerhardt | F04B 9/113 | 417/390 |
| 2003/0190237 A1 * | 10/2003 | Berger | F04B 11/0091 | 417/53 |
| 2004/0108273 A1 * | 6/2004 | Richardson | G01N 30/32 | 210/656 |
| 2004/0136833 A1 * | 7/2004 | Allington | F04B 1/02 | 417/44.1 |
| 2004/0164013 A1 * | 8/2004 | Takao | F04B 11/0075 | 210/198.2 |
| 2005/0023205 A1 * | 2/2005 | Hiraku | F04B 11/0058 | 210/198.2 |
| 2008/0135484 A1 * | 6/2008 | Hammer | G01N 30/92 | 210/656 |
| 2008/0179251 A1 * | 7/2008 | Davison | B01D 15/10 | 210/656 |
| 2008/0235081 A1 * | 9/2008 | Davison | G01N 35/00732 | 705/7.31 |
| 2008/0245136 A1 * | 10/2008 | Gerhardt | B01L 3/50273 | 73/61.56 |
| 2009/0166294 A1 * | 7/2009 | Davison | B01D 15/10 | 210/658 |
| 2009/0205409 A1 * | 8/2009 | Ciavarini | G01N 30/34 | 73/61.56 |
| 2010/0143155 A1 * | 6/2010 | Preiswerk | F04B 1/02 | 417/1 |
| 2011/0261642 A1 * | 10/2011 | Shreve | G01N 30/34 | 366/152.2 |
| 2012/0122731 A1 * | 5/2012 | Soh | B01L 3/502761 | 506/12 |
| 2012/0198919 A1 * | 8/2012 | Witt | G01N 30/34 | 73/53.01 |
| 2013/0008523 A1 * | 1/2013 | Witt | G01N 30/34 | 137/88 |
| 2013/0134095 A1 * | 5/2013 | Anderer | B01D 15/1878 | 210/656 |
| 2013/0330209 A1 * | 12/2013 | Joudrey | B01F 15/0404 | 417/54 |
| 2014/0251448 A1 * | 9/2014 | Witt | G05D 11/133 | 137/88 |
| 2014/0334251 A1 * | 11/2014 | Shreve | B01F 5/0644 | 366/336 |
| 2015/0219091 A1 * | 8/2015 | Jackson | F04B 49/06 | 417/12 |
| 2016/0153942 A1 * | 6/2016 | Yotani | G01N 30/16 | 73/61.55 |

FOREIGN PATENT DOCUMENTS

| | | | | |
|---|---|---|---|---|
| GB | 2432328 | * | 6/2009 | B01D 15/08 |
| JP | H07159388 | * | 6/1995 | G01N 30/02 |
| WO | 2006023828 | | 3/2006 | |

OTHER PUBLICATIONS

Dourdeville, T.A., WO 02/082103 A3, Oct. 17, 2002.*
Klaus, W., WO 2006087037 A1, Aug. 24, 2006.*
Jourdrey, K., WO 2012/099763 A1, Jul. 26, 2012.*
Combined Search adn Examination Report in counterpart Great Britain Application No. GB1500994.7, dated Jul. 9, 2015; 6 pages.

* cited by examiner

METHOD FOR HIGH PRESSURE GRADIENT CHROMATOGRAPHY USING PUMP STROKE CONTROL

RELATED APPLICATION

This application claims the benefit of the earlier filing date of U.S. Provisional Patent Application Ser. No. 61/936,385, filed Feb. 6, 2014 and titled "Method for High Pressure Gradient Chromatography Using Pump Stroke Control," the entirety of which is incorporated herein by reference.

FIELD OF THE INVENTION

The invention relates generally to high pressure gradient formation liquid chromatography. More particularly, the invention relates to a method for high pressure gradient formation based on controlling the pump strokes of solvent pumps.

BACKGROUND

In high pressure gradient liquid chromatography, the contribution of two or more solvents to the mobile phase changes over time. Generally, pumping systems for high pressure gradient liquid chromatography utilize parallel pumps to deliver multiple fluids in defined proportions to achieve a specified final fluid composition. Typically, each pump in the system is a combination of individual pump heads that are periodically refilled to maintain a constant fluid flow. The refilling process can cause disturbances or ripple in the flow and pressure of the delivered liquid due to a variety of factors, such as solvent compressibility and hydraulic inertia. If the refilling of a pump occurs during the pressure and flow disturbances resulting from the refilling of another pump, the solvent composition of the liquid delivered by the pumping system may not accurately match the desired solvent composition.

SUMMARY

In one aspect, a method of generating a flow having a composition gradient includes generating a plurality of pump strokes for a first pump in a system having at least the first pump and a second pump. Each of the pump strokes for the first pump has a volume contribution based on a relative contribution of a first liquid to a composition gradient for a flow. The pump strokes of the first pump are generated at a pump stroke frequency. A plurality of pump strokes is generated for the second pump. Each of the pump strokes for the second pump has a volume contribution based on a relative contribution of a second liquid to the composition gradient for the flow. The pump strokes for the second pump are generated at the pump stroke frequency and are interspersed in time with the pump strokes of the first pump. An initiation of each of the pump strokes of the second pump is offset in time relative to an initiation of a respective one of the pump strokes of the first pump such that variations in the flow rates of the first and second pumps based on the initiations of the pump strokes do not overlap in time.

In another aspect, a pump system includes a first pump, a second pump and a processor in communication with the first and second pumps. The first pump is configured to deliver volume contributions of a first liquid with each volume contribution occurring during a pump stroke of the first pump. The second pump is configured to deliver volume contributions of a second liquid with each volume contribution occurring during a pump stroke of the second pump. The processor is configured to control the first and second pumps to have a same pump stroke frequency and to be interspersed in time. The initiations of pump strokes of the first and second pumps are offset in time such that variations in the flow rates of the first and second pumps based on the initiations of the pump strokes do not overlap in time. The processor changes the volume contributions of the first and second pumps in time according to a predetermined composition gradient of a flow comprising the first and second liquids.

In yet another aspect, a computer program product for generating a flow having a composition gradient includes a computer readable storage medium. The computer readable storage medium has computer readable program code embodied therewith. The computer readable program code includes computer readable program code configured to generate a plurality of pump strokes for a first pump in a system having at least the first pump and a second pump. Each of the pump strokes for the first pump has a volume contribution based on a relative contribution of a first liquid to a composition gradient for a flow. The pump strokes for the first pump are generated at a pump stroke frequency. The computer readable program code further includes computer readable program code configured to generate a plurality of pump strokes for the second pump. Each of the pump strokes for the second pump has a volume contribution based on a relative contribution of a second liquid to the composition gradient for the flow. The pump strokes for the second pump are generated at the pump stroke frequency and are interspersed in time with the pump strokes of the first pump. An initiation of each of the pump strokes of the second pump is offset in time relative to an initiation of a respective one of the pump strokes of the first pump such that variations in the flow rates of the first and second pumps based on the initiations of the pump strokes do not overlap in time.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

DETAILED DESCRIPTION

Figure 1:
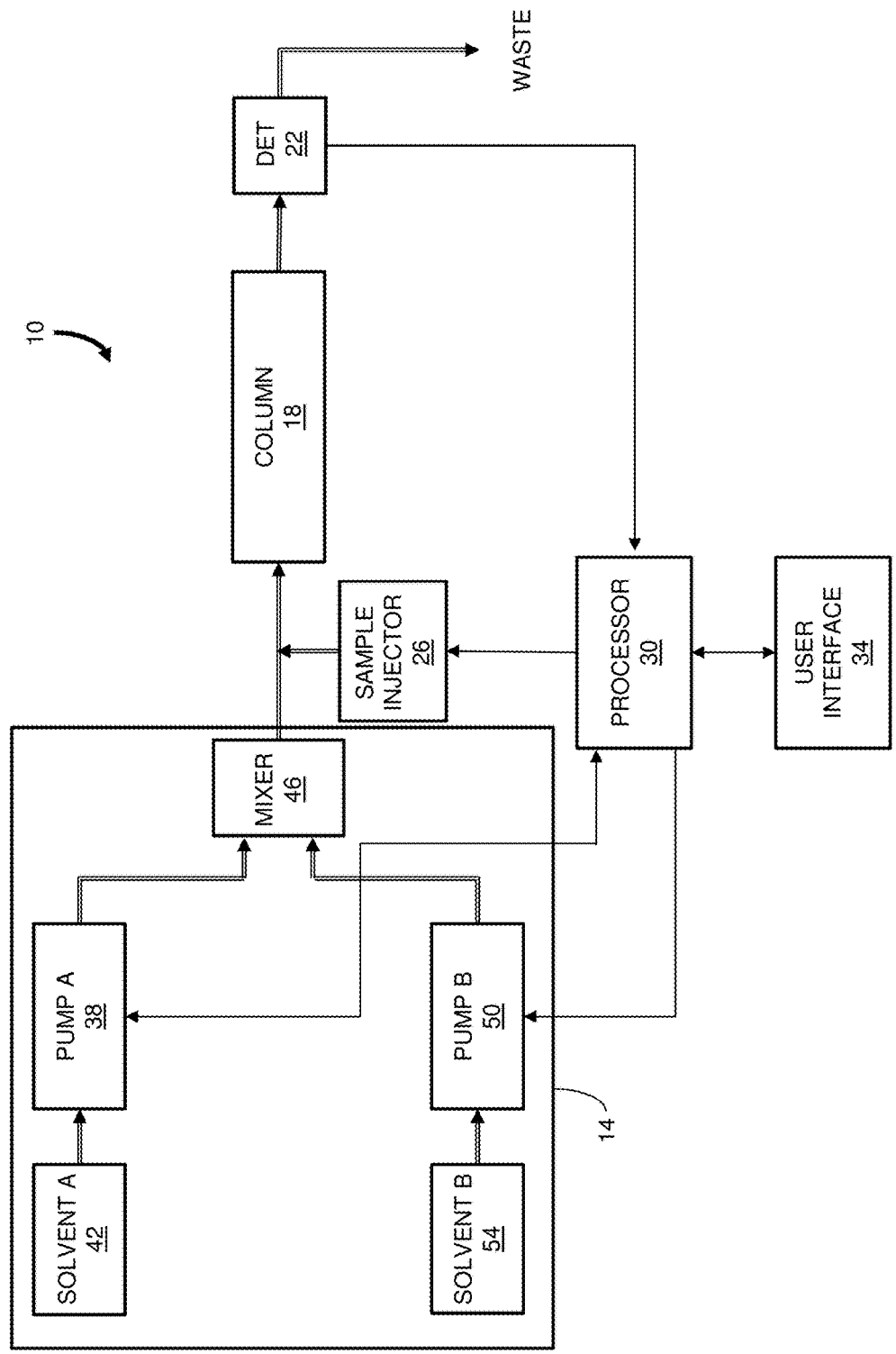
FIG. 1 is a block diagram of a liquid chromatography system that includes a binary solvent delivery system.

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

During a binary gradient liquid chromatography process, the solvent contributions from the two solvent pumps change over time. The changes in the solvent contributions are typically achieved by changing the pump stroke frequency (i.e., cycle time) of each solvent pump. Thus it is possible for one of the pumps to initiate a pump stroke in a pump head near or at the same time as the initiation of a pump stroke for a pump head in the other pump. Consequently, a "collision" can occur during which the variation (i.e., "ripple") in the flow rate of one pump occurring upon and soon after initiation of the pump stroke overlaps the ripple in the flow rate of the other pump following stroke initiation. The collision can degrade the compositional accuracy of the mobile phase gradient.

Some pump systems include a control system that anticipates a collision before it can occur. The control system reacts to this potential collision by shortening the stroke for the pump heads of one of the solvent pumps. This temporary modification of the pump strokes means that the following initiation of a pump stroke occurs earlier than if the nominal pump stroke were maintained. The process of shortening a pump stroke is repeated for potential future collisions to avoid their occurrence. The pump stroke may also be shortened for other conditions, such as high flow rates, high pressures and high compressibility solvents. Under such conditions, the opportunities to shorten the pump stroke to avoid collisions can be substantially reduced and, in some instances, sufficient opportunities may not exist to avoid collisions.

In brief overview, the invention relates to a method of generating a flow having a composition gradient. For example, the flow may be a mobile phase gradient used to perform liquid chromatography. In one embodiment, pump strokes for a first pump and pump strokes for a second pump occur at the same pump stroke frequency. In addition, the initiations of the pump strokes of the second pump are interspersed in time with the initiations of the pump strokes of the first pump. The initiations of the pump strokes of the two pumps are offset in time such that variations in the flow rates of the first and second pumps occurring upon initiation do not overlap in time. The pump stroke frequency can change over time as long as the initiations of the pump strokes of the second pump remain interspersed with the initiations of the pump strokes of the first pump.

The present teaching will now be described in more detail with reference to embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

A block diagram of a liquid chromatography system 10 is shown in FIG. 1 and includes a binary solvent delivery system 14 coupled to the inlet of a chromatographic column 18. The outlet of the column 18 is coupled to a detector 22. An injector valve 26 introduces a sample containing one or more sample components into the mobile phase provided by the binary solvent delivery system 14. The sample components adsorb to the stationary phase inside the column 18 to varying degrees. Components with a strong attraction to the stationary phase move more slowly through the column 18 than components with a weak attraction. Thus the components are separated according to the different speeds of movement through the column 18 and elute at different times. The component with the least affinity for the stationary phase elutes first, while the component with the greatest affinity for the stationary phase elutes last. The detector 22 analyzes the emerging stream by measuring a property that is related to the concentration and characteristic of chemical composition. By way of specific examples, the measured property can be refractive index or ultra-violet absorption.

A processor module 30 controls the operation of the binary solvent delivery system 14, sample injector 26 and detector 22. The processor module 30 can include one or more processing units and memory units, and may coordinate operational and control signals used to operate other components and subsystems of the liquid chromatography system 10. A user interface 34 in communication with the processor module 30 allows for various parameters of a chromatographic measurement to be defined and for output and display of operational and measurement data to a user.

In the illustrated binary solvent delivery system 14, a first pump 38 draws a first solvent A from a reservoir 42 and supplies the first solvent at a desired flow rate and pressure to a mixer 46. A second pump 50 draws a second solvent B from a second reservoir 54 and supplies the second solvent at a desired flow rate and pressure to the mixer 46. The solvents are blended at the mixer 46 to achieve a solvent mixture having desired mobile phase properties. The flow rate of each solvent can be adjusted to vary the composition of the solvent mixture over time. A variation in the solvent mixture over time is referred to as a solvent gradient or compositional gradient.

During a gradient liquid chromatography process, the relative contributions of the two solvents A and B to the mobile phase change in time. Typically, the contribution of a solvent is defined through the control of the flow rate of the corresponding solvent pump. Each pump stroke provides a volume of the solvent based on the displacement volume of the pump head during the pump stroke. This "volume contribution" may be different from the displacement volume of the pump head due to the compressibility of the solvent. Higher flow rates are achieved by operating the solvent pump at a higher pump stroke frequency while maintaining a fixed stroke volume. As used herein, the phrase "pump cycle" means the time between the initiations of two consecutive pump strokes.

Solvent pumps can be configured in a variety of ways. By way of a particular example, each solvent pump can be configured with two pump heads in a serial arrangement. Typically, one of the pump heads functions as a primary pump and the other pump head functions as an accumulator pump. In some configurations, the pump strokes of the primary and accumulator pumps operate with opposite phase. In an alternative configuration, pump heads are configured in a parallel arrangement with each pump head operating in opposite phase from the other pump head. One pump head delivers solvent while the other pump head is refilled with solvent.

Regardless of the configuration of pump heads, the flow rate of the solvent delivered by a pump 38, 50 can fluctuate at the beginning of a pump stroke due to a variety of factors, including compressibility of the solvent and hydraulic inertia. To generate a mobile phase gradient, the flow rates of the solvent pumps 38, 50 are changed over time. It is possible for one of the pumps 38 to initiate a stroke of one of its pump heads at nearly the same time as the initiation of a stroke in one of the pump heads of the other pump 50. Consequently, the ripple in the flow rates of the two pumps 38, 50 can overlap and adversely affect the compositional accuracy of the mobile phase gradient.

Figure 2:
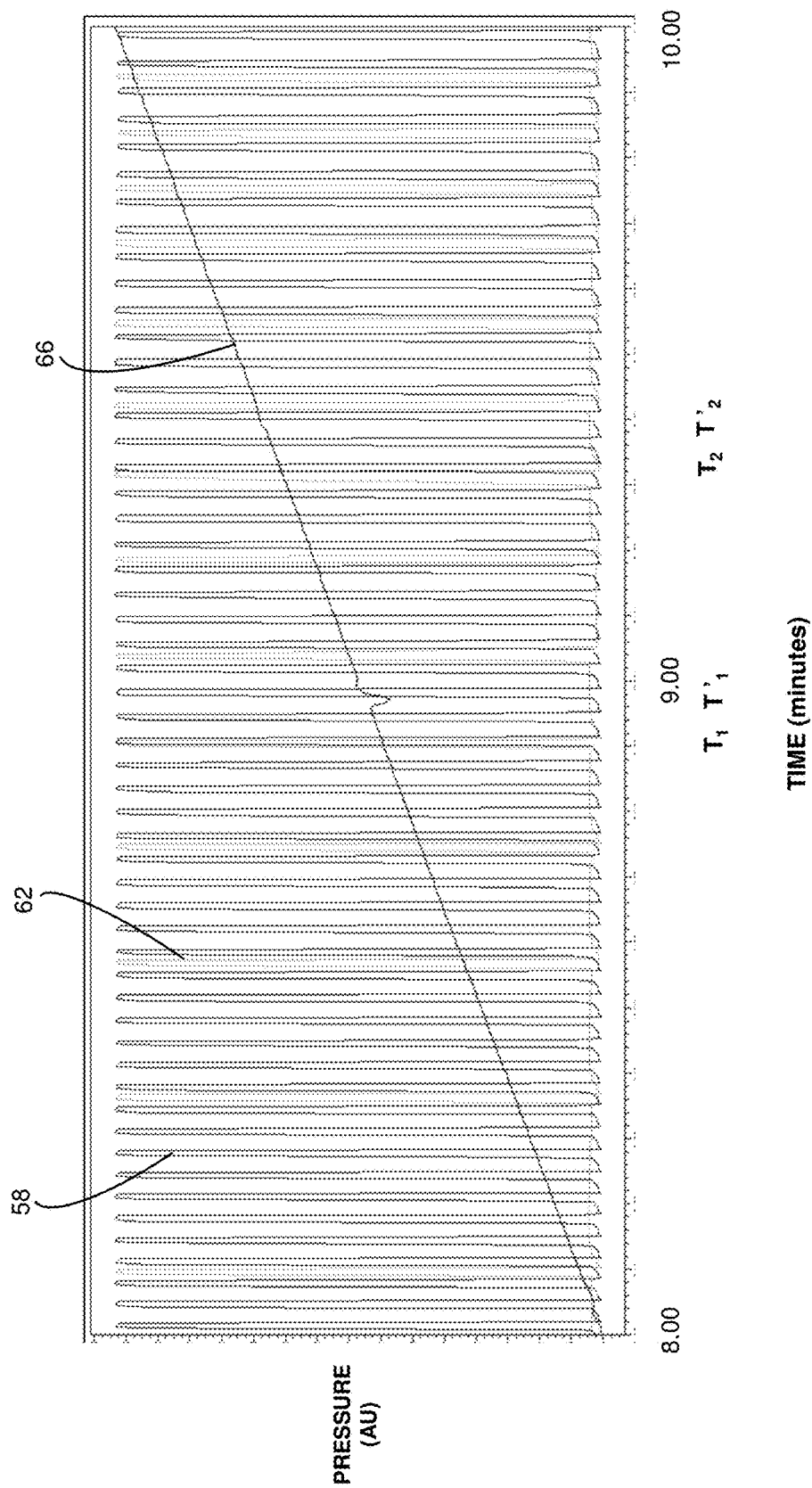
FIG. 2 is a graphical representation over time of the pressure pulses associated with the pump strokes of the primary pump heads of two solvent pumps operated to generate a mobile phase gradient.

Referring also to FIG. 2, a graphical representation of the pressure pulses associated with the pump strokes that transfer fluid from a primary pump head are shown as a function of time for each of the two solvent pumps 38, 50. Each pump stroke associated with pressure pulses 58 and 62 of a solvent pump 38 and 50, respectively, results in a volume contribution of the respective solvent to the mobile phase gradient to maintain the desired composition ratio for the solvents. The pump stroke frequency of solvent pump B 50 can be seen to be less than the pump stroke frequency of solvent pump A 38. The line 66 represents the amount of solvent B present in the solvent mixture. A gradient inaccuracy in the form of a variation from linearity is evident time $T'_1$ and a second smaller variation is evident at time $T''_2$. Each variation occurs at a respective time $T_1$ or $T_2$ when the initiations of pump strokes for the two solvent pumps are nearly coincident.

Figure 3:
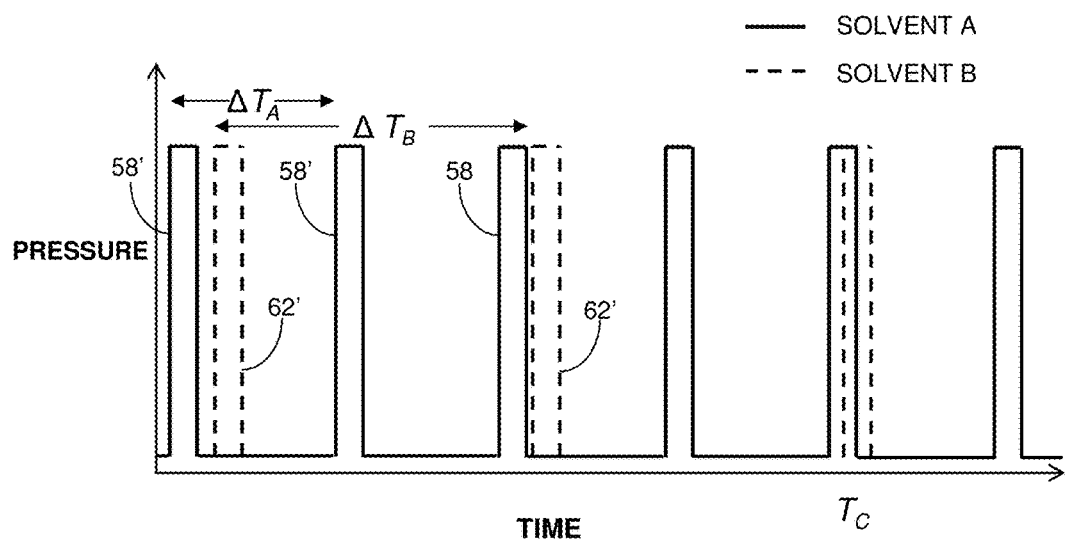
FIG. 3 is a simplified graphical depiction showing how the pump strokes of a solvent pump change in time with respect to the pump strokes of another solvent pump in a binary solvent pump system with a resulting collision.

FIG. 3 is a simplified graphical depiction over a smaller duration showing how the pump strokes 58' of one solvent pump change in time with respect to the pump strokes 62' of the other solvent pump in a binary solvent pump system. During each pump stroke, there are small flow disturbances that occur that can cause over delivery or under delivery of the volume contribution for that solvent for a brief time, leading to a composition error. The pump strokes 58' of solvent A are separated in time by a period $\Delta T_A$ and the pump strokes 62' of solvent B are separated in time by a period $\Delta T_B$. To increase the relative contribution of solvent B relative to that of solvent A, the pump stroke frequency of pump B is increased and the pump stroke frequency of pump A is decreased. The cycle period $\Delta T$ for each solvent pump is inversely proportional to the respective pump stroke frequency. Consequently, the cycle period $\Delta T_B$ for solvent B decreases with time while the cycle period $\Delta T_A$ for solvent A increases with time. One or more "collisions" of pump strokes for the two solvent pumps may occur during a gradient mobile phase run, such as shown at approximately time $T_C$.

Figure 4:
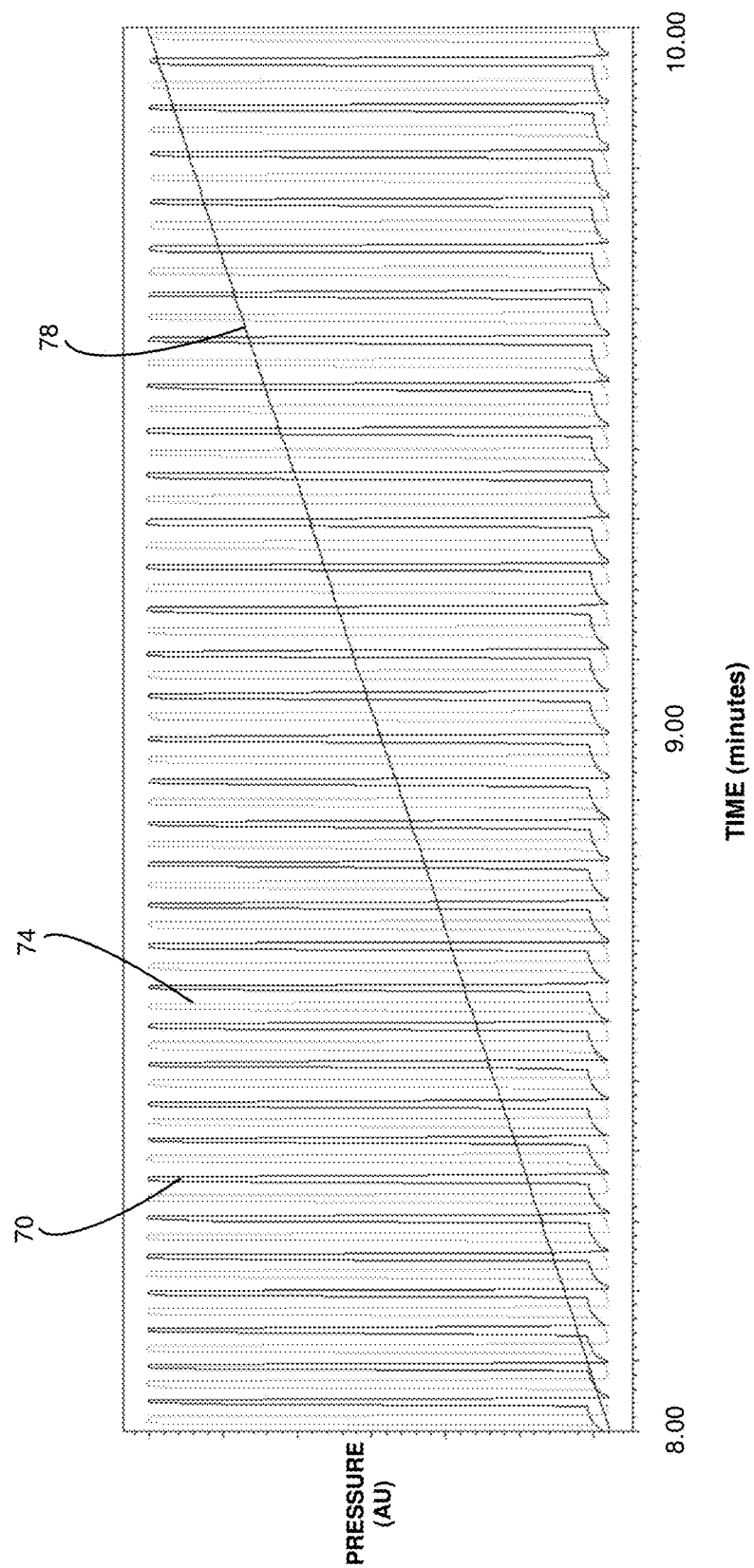
FIG. 4 shows an embodiment in which each pump stroke of one pump is initiated at a time between consecutive initiations of pump strokes of another pump so that the pump strokes of the two pumps are interspersed in time without collisions.

According to one embodiment of a method of generating a flow having a composition gradient, such as a mobile phase gradient, each pump is operated at substantially the same pump stroke frequency. Each stroke of one pump 38 is initiated at a time between consecutive stroke initiations of the other pump 50 so that the pump strokes and associated pressure pulses 74 and 78 of the two pumps are interspersed in time as shown in FIG. 4. The pump strokes are controlled over time to achieve the proper positioning in time of the pump strokes with respect to each other while maintaining the proper gradient composition 78. Preferably, the pump strokes of one pump 50 are initiated approximately midway in time between the initiation of an immediately preceding pump stroke and initiation of an immediately following pump stroke of the other pump 38. Alternatively, the initiation of a pump stroke of one pump can occur at any time over a range of suitable times between the initiations of consecutive pump strokes of the other pump. More specifically, the initiation of a pump stroke of one pump can occur at any time between the initiation of consecutive pump strokes of the other pump that avoids nearly simultaneous initiations for which the flow rate disturbances for the two pump strokes would overlap in time.

The initiations of pump strokes of the two solvent pumps can be interpreted as two pulse trains that are out of phase with each other. Preferably, the phase difference corresponding to the delay time between the two pulse trains is approximately 180° to maintain the initiations of pump strokes of one pump midway between the initiations of the pump strokes of the other pump and thereby allow for variations in controlled parameters, such as pump stroke frequency and pump stroke volume. Other phase differences are possible as long as sufficient operating margins are maintained to ensure that the initiations of the pump strokes for the two pumps do not occur close in time such that variations in the flow rates for the two pumps do not collide or overlap in time.

Figure 5:
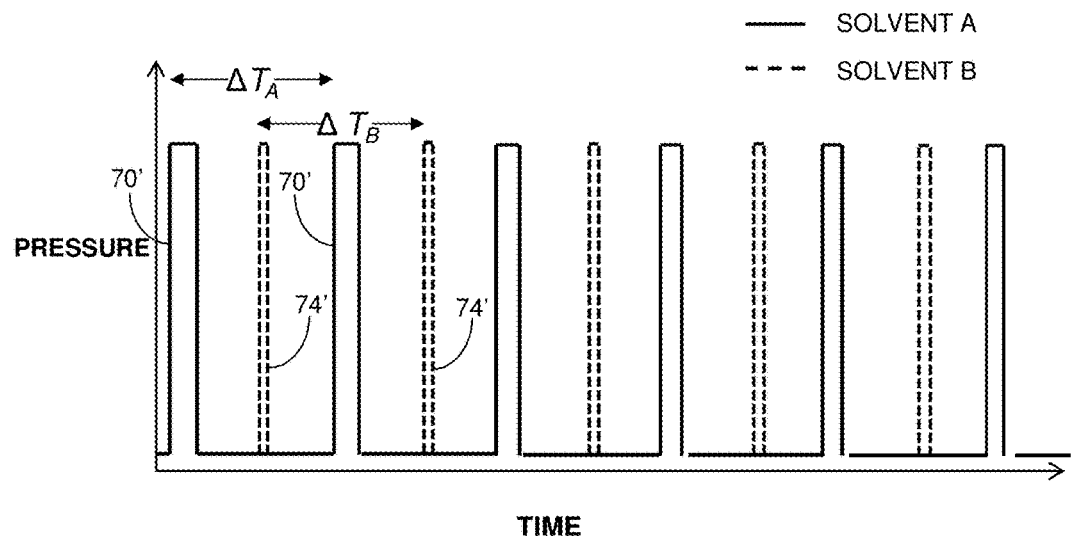
FIG. 5 is a simplified graphical depiction according to an embodiment of a method in which the pump strokes of two solvent pumps operate at the same pump stroke frequency and are interspersed in time.

FIG. 5 is a simplified graphical depiction of the pump strokes of two solvent pumps in accordance with an embodiment of a method of the invention. Volume contributions during the pump strokes 70' of solvent A gradually decrease over time while volume contributions during the pump strokes 74' of solvent B are gradually increased. Unlike traditional techniques for generating a binary mobile phase gradient, such as shown in FIG. 2, the phase defined between the initiations of the pump strokes of the two pumps remains substantially constant over the duration of the mobile phase gradient run. In an alternative embodiment, the pump stroke frequency for the two pumps can change during the gradient run; however, the relative phase between the pump strokes of the two pumps remains constant.

Although described above primarily with respect to binary pump systems, the method of the invention can be used with pump systems using three or more pumps. For example, a three pump system is operated such that all the pumps operate at the same pump stroke frequency and each pulse train has a different phase. More specifically, the phases of the pump strokes for two of the pumps would preferably be 120° and 240° with reference to the phase of the pump strokes for the third pump.

In some mobile phase gradients, there can be a period of time when the volume contribution from one of the pumps is substantially less than the volume contribution from the other pump. For example, the contribution ratio of the solvents may be a few percent or less. There is a minimum time for a transfer from the pump heads therefore it can be advantageous to operate the greater contribution solvent pump at a pump stroke frequency that is an integer multiple of the pump stroke frequency of the lower contribution solvent pump.

According to another embodiment of a method of generating a flow having a composition gradient, one pump is operated at a pump stroke frequency that is an integer multiple of the pump stroke frequency of the other pump. For example, a "faster" pump contributing a substantially higher flow rate can be operated at twice the pump stroke frequency of a "slower" pump contributing at a lesser flow rate. In this circumstance, two pump strokes of the faster pump occur between consecutive occurrences of pump strokes for the slower pump. The timing of each pump stroke of the slower pump is controlled so that the pump stroke is initiated approximately midway between an initiation of an immediately preceding pump stroke and an initiation of an immediately following pump stroke of the faster pump.

More generally, the ratio of the pump stroke frequencies does not have to be a constant over the duration of the gradient run as long as each pump stroke of the slower pump is initiated between the initiations of an immediately preceding pump stroke and an immediately following pump stroke of the faster pump.

While the invention has been shown and described with reference to specific embodiments, it should be understood by those skilled in the art that various changes in form and detail may be made therein without departing from the spirit and scope of the invention as recited in the accompanying claims.

What is claimed is:

1. A method of generating a flow having a composition gradient, the method comprising:
    generating a plurality of pump strokes for a first pump in a system having at least the first pump and a second pump, each of the pump strokes for the first pump delivering a volume contribution of a first liquid-in response to a displacement volume of the first pump, the pump strokes of the first pump being generated at a pump stroke frequency; and
    generating a plurality of pump strokes for the second pump, each of the pump strokes for the second pump delivering a volume contribution of a second liquid in response to a displacement volume of the second pump, the pump strokes for the second pump being generated at the pump stroke frequency and being interspersed in time with the pump strokes of the first pump, an initiation of each of the pump strokes of the second pump being offset in time relative to an initiation of a respective one of the pump strokes of the first pump such that variations in the flow rates of the first and second pumps based on the initiations of the pump strokes do not overlap in time, wherein the volume contributions of the pump strokes of each of the first and second pumps are controlled according to a predetermined composition gradient of a flow comprising the first and second liquids.

2. The method of claim 1 wherein each of the pump strokes of the second pump is initiated midway in time between an initiation of an immediately preceding pump stroke of the first pump and an initiation of an immediately following pump stroke of the first pump.

3. The method of claim 1 wherein, for each of the pump strokes of the second pump, an initiation of the pump stroke occurs after an initiation of the pump stroke of the first pump by a constant delay time.

4. The method of claim 1 wherein a phase difference between a sequence of consecutive pump strokes for the first pump and a sequence of consecutive pump strokes for the second pump is approximately 180°.

5. The method of claim 1 wherein the first and second liquids are solvents and wherein the flow is a mobile phase gradient comprising the solvents.

6. A pump system, comprising:
    a first pump configured to deliver volume contributions of a first liquid, each of the volume contributions occurring during a pump stroke of the first pump and being responsive to a displacement volume of the first pump;
    a second pump configured to deliver volume contributions of a second liquid, each of the volume contributions occurring during a pump stroke of the second pump and being responsive to a displacement volume of the second pump; and
    a processor in communication with the first and second pumps, the processor configured to control the first and second pumps to have a same pump stroke frequency and to be interspersed in time so that initiations of the pump strokes of the first and second pumps are offset in time such that variations in the flow rates of the first and second pumps based on the initiations of the pump strokes do not overlap in time, the processor changing the volume contributions of the first and second pumps in time according to a predetermined composition gradient of a flow comprising the first and second liquids.

7. The pump system of claim 6 wherein the first and second pumps are solvent pumps and wherein the flow is a mobile phase gradient.

8. The pump system of claim 7 further comprising a mixer having an inlet in communication with the first pump to receive the solvent from the first pump, an inlet in communication with the second pump to receive the solvent from the second pump, and an outlet to provide the flow comprising the first and second solvent.

9. The pump system of claim 6 wherein each of the first and second pumps is configured with two pump heads in a serial arrangement and wherein one of the pump heads is a primary pump and the other of the pump heads is an accumulator pump.

10. The pump system of claim 6 wherein each of the first and second pumps is configured with two pump heads in a parallel arrangement and wherein the pump strokes of one of the pump heads is configured to operate in opposite phase from the pump strokes of the other pump head.

11. The pump system of claim 6 wherein the processor is configured to change the pump stroke frequency of the first and second pumps.

12. The pump system of claim 6 wherein the processor is configured to control the first and second pumps so that each initiation of the pump strokes of the second pump occurs approximately midway between each initiation of an immediately preceding pump stroke of the first pump and each initiation of an immediately following pump stroke of the first pump.

13. The pump system of claim 6 wherein the processor is configured to control the first and second pumps so that for each of the pump strokes of the second pump, an initiation of the pump stroke occurs after an initiation of the pump stroke of the first pump by a constant delay time.

14. The pump system of claim 6 wherein the processor is configured to control the first and second pumps so that a phase difference between a sequence of consecutive pump strokes for the first pump and a sequence of consecutive pump strokes for the second pump is approximately 180°.

15. A computer program product for generating a flow having a composition gradient, comprising:
    a non-transitory computer readable storage medium having computer readable program code embodied therewith, when executed on a computer, the computer readable program code performing:
    generating a plurality of pump strokes for a first pump in a system having at least the first pump and a second pump, each of the pump strokes for the first pump delivering a volume contribution of a first liquid in response to a displacement volume of the first pump, the pump strokes for the first pump being generated at a pump stroke frequency; and
    generating a plurality of pump strokes for the second pump, each of the pump strokes for the second pump delivering a volume contribution of a second liquid in response to a displacement volume of the second pump, the pump strokes for the second pump being generated at the pump stroke frequency and being interspersed in time with the pump strokes of the first pump, an initiation of each of the pump strokes of the second pump being offset in time relative to an initiation of a respective one of the pump strokes of the first pump such that variations in the flow rates of the first and second pumps based on the initiations of the pump strokes do not overlap in time, wherein the volume contributions of the pump strokes of each of the first and second pumps are controlled according to a predetermined composition gradient of a flow comprising the first and second liquids.

* * * * *